United States Patent
Rosenbaum et al.

(10) Patent No.: US 8,318,001 B2
(45) Date of Patent: *Nov. 27, 2012

(54) 110 NEUTRAL BASE OIL WITH IMPROVED PROPERTIES

(75) Inventors: John M. Rosenbaum, Richmond, CA (US); Brent K. Lok, San Francisco, CA (US); Kathy A. Helling, Santa Rosa, CA (US); Ryan J. Schexnaydre, Richmond, CA (US); Scott C. Deskin, Alameda, CA (US); Susan M. Abernathy, Hercules, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 221 days.

This patent is subject to a terminal disclaimer.

(21) Appl. No.: 12/481,827

(22) Filed: Jun. 10, 2009

(65) Prior Publication Data

US 2010/0081590 A1    Apr. 1, 2010

Related U.S. Application Data

(60) Provisional application No. 61/101,674, filed on Oct. 1, 2008.

(51) Int. Cl.
*C10M 105/04* (2006.01)
*C10M 169/04* (2006.01)
(52) U.S. Cl. .............. 208/18; 208/19; 508/110
(58) Field of Classification Search ........ 508/110; 208/18

See application file for complete search history.

(56) References Cited

U.S. PATENT DOCUMENTS

| | | | |
|---|---|---|---|
| 2,489,300 | A | 11/1949 | Leyda |
| 4,519,925 | A | 5/1985 | Smith |
| 7,141,157 | B2 * | 11/2006 | Rosenbaum et al. ........... 208/18 |
| 7,144,497 | B2 | 12/2006 | Lok et al. |
| 7,374,658 | B2 * | 5/2008 | Rosenbaum et al. ........... 208/18 |
| 7,655,132 | B2 * | 2/2010 | Miller et al. .................. 208/18 |
| 7,687,445 | B2 * | 3/2010 | Rosenbaum et al. ......... 508/591 |
| 7,846,880 | B2 * | 12/2010 | Rosenbaum et al. ......... 508/110 |
| 2004/0043910 | A1 | 3/2004 | Lok et al. |
| 2004/0118744 | A1 | 6/2004 | Daniel et al. |
| 2004/0178118 | A1 | 9/2004 | Rosenbaum et al. |
| 2005/0098476 | A1 | 5/2005 | Miller |

(Continued)

FOREIGN PATENT DOCUMENTS

WO    01/34735    5/2001

OTHER PUBLICATIONS

ConocoPhillips, Pure Performance Base Oils Specifications, May 2004.

(Continued)

*Primary Examiner* — Ellen McAvoy
(74) *Attorney, Agent, or Firm* — Jeffrey M. McQuiston; Susan M. Abernathy

(57) ABSTRACT

We provide a base oil comprising hydrocarbons with consecutive numbers of carbon atoms. The base oil has a boiling range from 700 to 925° F. (371 to 496° C.), a VI from 105 to 119, and either a Noack volatility less than 18 wt % or a CCS VIS at −25° C. less than 1500 mPa·s. The base oil may have a ratio of Noack Volatility to CCS VIS at −25° C. multiplied by 100 from 0.80 to 1.55.

20 Claims, 2 Drawing Sheets

U.S. PATENT DOCUMENTS

| | | | |
|---|---|---|---|
| 2005/0261145 A1 | 11/2005 | Rosenbaum et al. | |
| 2006/0027486 A1 | 2/2006 | Rosenbaum et al. | |
| 2008/0029431 A1 | 2/2008 | Alexander et al. | |
| 2008/0110797 A1* | 5/2008 | Fyfe et al. | 208/18 |
| 2008/0116108 A1* | 5/2008 | Zhang et al. | 208/18 |
| 2008/0140366 A1 | 6/2008 | Gao et al. | |
| 2008/0149529 A1 | 6/2008 | Rosenbaum et al. | |
| 2008/0171675 A1* | 7/2008 | Yeh et al. | 508/110 |
| 2009/0036333 A1* | 2/2009 | Scholier et al. | 508/110 |
| 2009/0036338 A1* | 2/2009 | Hee et al. | 508/506 |
| 2009/0062164 A1* | 3/2009 | Hee et al. | 508/110 |
| 2009/0062166 A1* | 3/2009 | Hee et al. | 508/459 |
| 2009/0143261 A1* | 6/2009 | Takeoka et al. | 508/110 |
| 2009/0149357 A1* | 6/2009 | McGeehan | 508/110 |

OTHER PUBLICATIONS

Evergreen Base Oil 110 Specifications. http://www.evergreenoil.com/products/Rerefines Base Oils.htm.

John J. McKetta et al., "Asphalt Emulsion to Blending," Encyclopedia of Chemical Processing and Design, 1997, pp. 454-471, vol. 4,Marcel Dekker, Inc., New York.

John J. McKetta et al., Encyclopedia of Chemical Processing and Design, 1997, pp. 473-491, vol. 4,Marcel Dekker, Inc., New York.

U.S. Appl. No. 12/047,887, Process for Improving Lubricating Qualities of Low Quaility Base Oils, John M. Rosenbaum et al., filed Mar. 13, 2003.

* cited by examiner

110 NEUTRAL BASE OIL WITH IMPROVED PROPERTIES

This application claims the benefit of provisional Application No. 61/101,674, filed Oct. 1, 2008, herein incorporated in its entirety.

This application is related to co-filed patent applications titled "A Process to Make a 110 Neutral Base Oil with Improved Properties", "A Method for Predicting a Property of a Base Oil", "A 170 Neutral Base Oil with Improved Properties", and "A Process to Manufacture a Base Stock and a Base Oil Manufacturing Plant"; herein incorporated in their entireties.

FIELD OF THE INVENTION

This invention is directed to base oils having consecutive numbers of carbon atoms and a defined boiling range, with improved Noack volatility, improved CCS viscosity, or a desired ratio thereof. This invention is also directed to a process to make the base oil, and a base oil made by the process of removing a lower boiling fraction from a selected original base oil. This invention is also directed to a method for predicting a property of a base oil.

Chevron 110RLV is a new base oil with improved properties. Chevron 100R, 150R, and Chevron 220R are commercial Group II base oils. Chevron 4R, 5R, and 7R are commercial highly paraffinic unconventional base oils. Chevron 4R and Chevron 7R are Group III base oils, and Chevron 5R is a Group II base oil.

Figure 2:
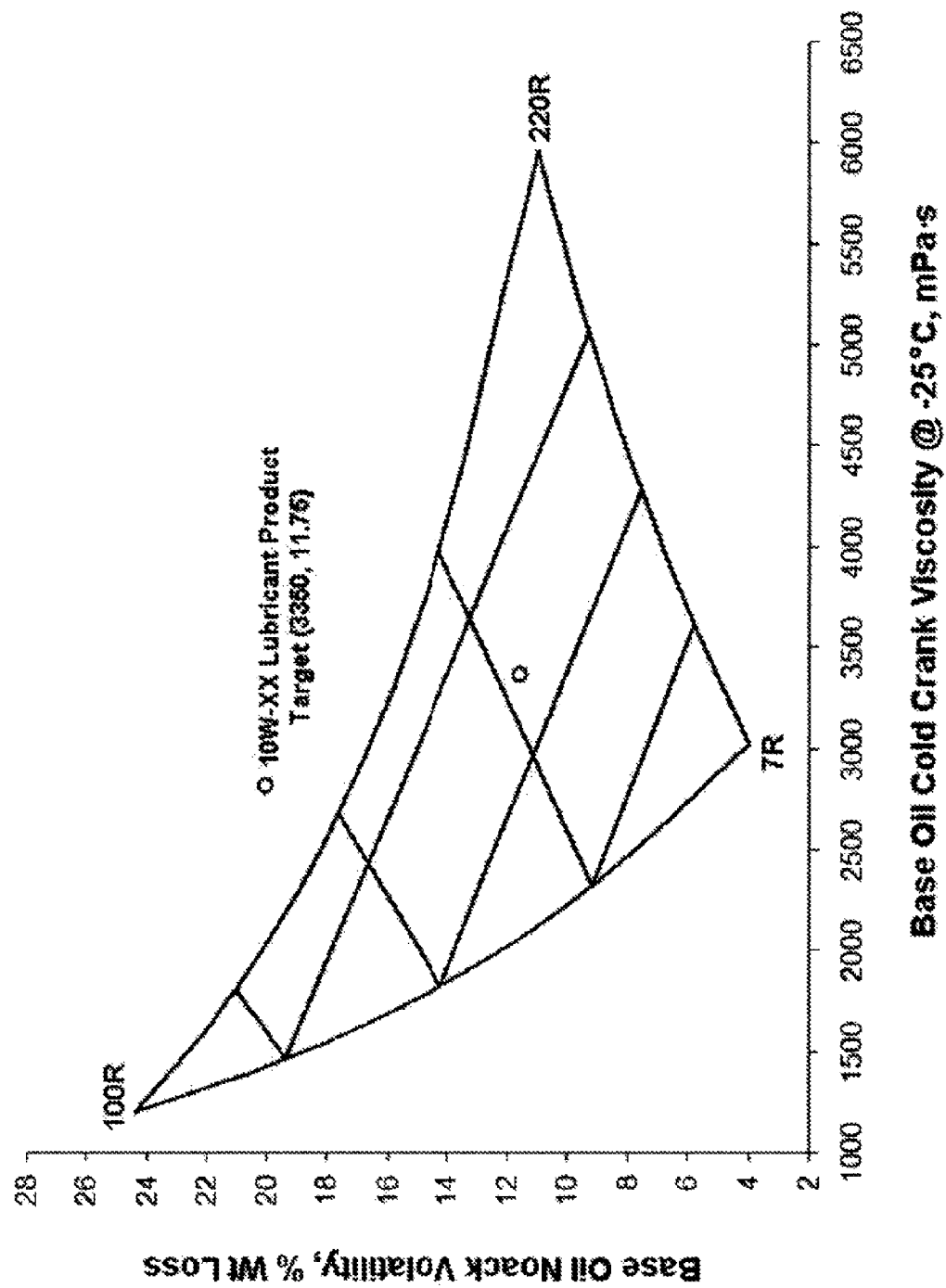

FIG. 2 illustrates a blend chart having a first point defined by the CCS VIS and Noack volatility of Chevron 100R. The blend chart has a second point defined by the CCS VIS and Noack volatility of Chevron 7R. The blend chart has a third point defined by the CCS VIS and Noack volatility of Chevron 220R. Curves are drawn between the three points. A target point of a CCS VIS of 3342 and a Noack volatility of 11.73 is placed on the chart. The chart instructs a user how much of each of the three base oils may be blended to meet the target point properties.

DETAILED DESCRIPTION OF THE INVENTION

Definitions:

The term "comprising" means including the elements or steps that are identified following that term, but any such elements or steps are not exhaustive, and an embodiment may include other elements or steps.

"Consecutive numbers of carbon atoms" means that the base oil has a distribution of hydrocarbon molecules over a range of carbon numbers, with every number of carbon numbers in-between. For example, the base oil may have hydrocarbon molecules ranging from C22 to C36 or from C30 to C60 with every carbon number in-between. The hydrocarbon molecules of the base oil differ from each other by consecutive numbers of carbon atoms, as a consequence of the waxy feed used to make the base oil also having consecutive numbers of carbon atoms. For example, in the Fischer-Tropsch hydrocarbon synthesis reaction, the source of carbon atoms is CO and the hydrocarbon molecules are built up one carbon atom at a time. Petroleum-derived waxy feeds have consecutive numbers of carbon atoms. In contrast to an oil based on polyalphaolefin, the molecules of a base oil made from a waxy feed and having consecutive numbers of carbon atoms have a more linear structure, comprising a relatively long backbone with short branches. The classic textbook description of a polyalphaolefin is a star-shaped molecule, and in particular tridecane, which is illustrated as three decane molecules attached at a central point. While a star-shaped molecule is theoretical, nevertheless polyalphaolefin molecules have fewer and longer branches that the hydrocarbon molecules that make up the base oil disclosed herein.

A "base stock" is a lubricant component that is produced by a single manufacturer to the same specifications (independent of feed source or manufacturers location): that meets the same manufacturer's specification; and that is identified by a unique formula, product identification number, or both. Base stocks may be manufactured using a variety of different processes including but not limited to distillation, solvent refining, hydrogen processing, oligomerization, esterification, and rerefining.

A "base oil" is a base stock or blend of different base stocks. It is suitable for blending with additives into finished lubricants meeting desired specifications.

A "base stock slate" is a product line of base stocks that have different viscosities but are in the same base stock grouping and from the same manufacturer.

A "light neutral base oil" has a boiling range of approximately 650° F. to 900° F. (343° C. to 482° C.), a pour point not greater than about −5° C., and a kinematic viscosity at 100° C. of about 4 to about 5 $mm^2/s$.

A "highly paraffinic unconventional base oil" is a Group II or Group III base oil having greater than 72% paraffinic carbon and less than 30% naphthenic carbon by n-d-M analysis.

N-d-M analysis is done by ASTM D3238-95 (Reapproved 2005) with normalization. ASTM D3238-95 (Reapproved 2005) is the Standard Test Method for Calculation of Carbon Distribution and Structural Group Analysis of Petroleum Oils by the n-d-M Method. This method is for "olefin free" feedstocks which are assumed in this application to mean that that olefin content is 2 wt % or less. The normalization process consists of the following: A) If the Ca value is less than zero, Ca is set to zero, and Cn and Cp are increased proportionally so that the sum is 100%. B) If the Cn value is less than zero, Cn is set to zero, and Ca and Cp are increased proportionally so that the sum is 100%; and C) If both Cn and Ca are less than zero, Cn and Ca are set to zero, and Cp is set to 100%.

Test Method Descriptions:

"Boiling range" is the 5 wt % boiling point to the 95 wt %, inclusive of the end points, as measured by ASTM D 6352-04 and referred to herein as SimDist. A hydrocarbon with a boiling range of 700 to 900° F., for example has a 5 wt % boiling point greater than 700° F. and a 95 wt % boiling point less than 900° F.

"Kinematic viscosity" is a measurement in $mm^2/s$ of the resistance to flow of a fluid under gravity, determined by ASTM D445-06.

"Viscosity index" (VI) is an empirical, unit-less number indicating the effect of temperature change on the kinematic viscosity of the oil. The higher the VI of an oil, the lower its tendency to change viscosity with temperature. VI is measured according to ASTM D 2270-04.

"Cold-cranking simulator apparent viscosity" (CCS VIS) is a measurement in millipascal seconds, mPa·s, to measure the viscometric properties of lubricating base oils under low temperature and low shear. CCS VIS is determined by ASTM D 5293-04.

"Noack volatility" is defined as the mass of oil, expressed in weight %, which is lost when the oil is heated at 250° C. with a constant flow of air drawn through it for 60 minutes, measured according to ASTM D5800-05, Procedure B.

"Pour point" is a measurement of the temperature at which a sample of base oil will begin to flow under certain carefully controlled conditions, which can be determined as described in ASTM D 5950-02.

"Flash point" is a measure of the tendency of the base oil to form a flammable mixture with air under controlled laboratory conditions. It is measured using a Cleveland open cup apparatus (manual or automated), by ASTM D 92-05a.

"Oxidator BN" measures the response of a base oil in a simulated application. High values, or long times to absorb one liter of oxygen, indicate good stability. Oxidator BN can be measured via a Domte-type oxygen absorption apparatus (R. W. Domte "Oxidation of White Oils," Industrial and Engineering Chemistry, Vol. 28, page 26, 1936), under 1 atmosphere of pure oxygen at 340° F. The time, in hours, to absorb 1000 ml of $O_2$ by 100 grams of oil is reported. In the Oxidator BN test, 0.8 ml of catalyst is used per 100 grams of oil. The catalyst is a mixture of soluble metal-naphthenates simulating the average metal analysis of used crankcase oil. The additive package is 80 millimoles of zinc bispolypropylenephenyldithiophosphate per 100 grams of oil.

"Weight percent aromatics" gives an indication of the UV and oxidation stability of a base oil. It can be measured by HPLC-UV. In one embodiment, the test is conducted using a Hewlett Packard 1050 Series Quaternary Gradient High Performance Liquid Chromatography (HPLC) system, coupled with a HP 1050 Diode-Array UV-Vis detector interfaced to an HP Chem-station. Identification of the individual aromatic classes in the base oil can be made on the basis of the UV spectral pattern and the elution time. The amino column used for this analysis differentiates aromatic molecules largely on the basis of their ring-number (or double-bond number). Thus, the single ring aromatic containing molecules elute first, followed by the polycyclic aromatics in order of increasing double bond number per molecule. For aromatics with similar double bond character, those with only alkyl substitution on the ring elute sooner than those with naphthenic substitution. Unequivocal identification of the various base oil aromatic hydrocarbons from their UV absorbance spectra can be accomplished recognizing that their peak electronic transitions are all red-shifted relative to the pure model compound analogs to a degree dependent on the amount of alkyl and naphthenic substitution on the ring system. Quantification of the eluting aromatic compounds can be made by integrating chromatograms made from wavelengths optimized for each general class of compounds over the appropriate retention time window for that aromatic. Retention time window limits for each aromatic class can be determined by manually evaluating the individual absorbance spectra of eluting compounds at different times and assigning them to the appropriate aromatic class based on their qualitative similarity to model compound absorption spectra.

Base Oil

We have developed an improved base oil comprising hydrocarbons with consecutive numbers of carbon atoms. In one embodiment, the base oil has a boiling range from 700 to 925° F. (371 to 496° C.), a VI from 105 to 119, and a Noack volatility less than 18 wt %.

In a second embodiment, the base oil has a boiling range from 700 to 925° F. (371 to 496° C.), a VI from 105 to 119, and a CCS VIS at −25° C. less than 1500 mPa·s.

In a third embodiment, the base oil has a boiling range from 700 to 925° F. (371 to 496° C.), a CCS VIS at −25° C. of at least 1100 mPa·s, and a ratio of Noack volatility to CCS VIS at −25° C. multiplied by 100 from 0.80 to 1.55.

The base oil has a VI that is less than 120, such that the base oil falls with the VI range of An API Group II base oil. In some embodiments the VI is from 105 to 119, or from 105 to 115, such as from 107 to 115, 107 to 113, 109 to 114, or 110 to 115.

The base oil has a low Noack volatility, generally less than 25 wt % or less than 20 wt %. In some embodiments the Noack volatility is less than 18 wt %, less than 17 wt %, or less than 16.5 wt %.

In one embodiment the base oil has an Oxidator BN that is greater than 18, 20, 22, or 24 hours. In some embodiments the Oxidator BN of the base oil is higher than the original Oxidator BN of an original base oil from which the base oil is made.

In one embodiment the base oil has a high flash point, such as greater than 210° C., greater than 215° C., or greater than 220° C. Generally, the base oil has a flash point less than 275° C.

In one embodiment the base oil has a low wt % total aromatics, such as less than 0.20 wt %, less than 0.10 wt %, or less than 0.05 wt %.

One feature of the base oil is that it can be blended into a wide variety of high quality finished lubricants by blending the base oil with one or more additives. Examples of finished lubricants that can be made from the base oil include engine oils, greases, heavy duty motor oils, passenger car motor oils, transmission and torque fluids, natural gas engine oils, marine lubricants, railroad lubricants, aviation lubricants, food processing lubricants, paper and forest products, metalworking fluids, gear lubricants, compressor lubricants, turbine oils, hydraulic oils, heat transfer oils, barrier fluids, and other industrial products. In one embodiment the base oil can be blended into a multigrade engine oil. Examples of multigrade engine oils that can be blended with the base oil are 5W-XX, 10W-XX, and 15W-XX, wherein XX is selected from the group consisting of 20, 30, 40, 50, and 60.

The base oil may additionally comprise a second base oil. In one embodiment the second base oil is a Group II base oil. Group II, Group III, and Group IV base oils are defined in Appendix E of the API 1509 specification, April 2008. A Group II base oil has greater than or equal to 90 percent saturates and less than or equal to 0.03 percent sulfur and has a VI greater than or equal to 80 and less than 120. A Group III base oil has greater than or equal to 90 percent saturates and less than or equal to 0.03 percent sulfur and has a VI greater than or equal to 120. A Group IV base oil is a polyalphaolefin. The second base oil, for example can be one having a kinematic viscosity at 40° C. from 40.00 to 46.00 mm$^2$/s, such as a 220 neutral.

In some embodiments the base oil additionally comprises a second base oil. In one embodiment the base oil contains less than 20 wt %, less than 10 wt % Group III or Group IV base oil, less than 5 wt % Group III or Group IV base oil, or no Group III or Group IV base oil. In another embodiment the base oil contains less than 20 wt %, less than 10 wt %, or no highly paraffinic unconventional base oil. One example of a base oil that can be made without any Group III or Group IV base oil, is base oil having a kinematic viscosity at 40° C. from 28.00 to 32.00 mm²/s. This base oil could be referred to as a 150 neutral base oil. This 150 neutral base oil has perfect properties for blending with additives, and even with no other base oils, into engine oils. It can be blended into 10W engine oils that meet modern specifications, including low Noack volatility. Examples of modern specifications that these engine oils can meet are the ACEA 2007 limits for A3/B3, A3/B4, and A5/B5 for gasoline and diesel engine oils.

In one embodiment the base oil can be blended into a 5W grade, a 10W grade, and a 15W grade engine oil without a high amount of Group III or Group IV base oil in the blend. In another embodiment the base oil can be blended into a 5W grade, a 10W grade, and a 15W grade without a high amount of highly paraffinic unconventional base oil. Group III, Group IV, and highly paraffinic unconventional base oils are often considerably more expensive than other Group II base oils. In another embodiment, the 5W, 10W and 15W grades are all multigrade engine oils. In the context of this disclosure, a high amount of Group III or Group IV base oil is considered to be greater than 20 wt %, or in some embodiments a high amount can be greater than 10 wt %. In one embodiment the base oil can be blended into a 5W grade, a 10W grade, and a 15W grade engine oil without any Group III or Group IV base oil in the blend. In another embodiment the base oil can be blended into a 5W grade, a 10W grade, and a 15W grade engine oil without any highly paraffinic unconventional base oil. 5W, 10W, and 15W grades and multigrade 5W-XX, 10W-XX, and 15W-XX engine oil viscosities are defined by the SAE J300 specification, published Nov. 1, 2007.

Process to Manufacture Base Oil

We provide a process to manufacture a base oil, comprising selecting an original base oil having an original VI from 95 to 115, an original Noack volatility from 20 to 30 wt %, and an original CCS VIS at −25° C. from 1100 to 1500 mPa·s. We remove a lower boiling fraction from the original base oil, whereby a base oil is made having a kinematic viscosity at 100° C. from 4.2 to 4.6 mm²/s, a VI that is at least 4 higher than the original VI, a Noack volatility that is at least 3 wt % lower than the original Noack volatility, and a CCS VIS at −25° C. that is within 200 mPa·s of the original CCS VIS at −25° C.

In one embodiment, the base oil has a ratio of Noack volatility to CCS VIS at −25° C. multiplied by 100 within a desired range. The desired range may be from 0.80 to 1.55, from 0.90 to 1.40, from 0.90 to 1.30, or from 1.0 to 1.30.

In one embodiment, the original base oil has an original kinematic viscosity at 100° C. from 3.75 to 4.45 mm²/s. When the lower boiling fraction is removed this raises the kinematic viscosity of the base oil. In one embodiment the base oil has a kinematic viscosity at 100° C. from 4.05 to 4.75 mm²/s.

In one embodiment the lower boiling fraction is all of the hydrocarbons in the original base oil boiling below a certain temperature, such as for example 625° F., 650° F., 655° F., or 660° F. The lower boiling fraction is removed by carefully controlled vacuum distillation having a tower top temperature, a tower bottom temperature, a tower top pressure and a tower bottom pressure that are selected to remove all of the hydrocarbons in the original base oil boiling below the certain temperature. Various different types of vacuum distillation control systems may be employed, such as those taught in U.S. Pat. No. 3,365,386, 4,617,092, or 4,894,145; in order to provide the highest yields of desired fractions and exact cut points.

In one embodiment the VI of the base oil is at least 5 higher than the original VI of the original base oil. For example, in this embodiment if the original VI is 105, the VI of the base oil is at least 110. The VI of the base oil is less than 120, such that the base oil is an API Group II base oil. In one embodiment, the base oil has a VI from 105 to 119, or 105 to 115.

The Noack volatility of the base oil is at least 3 wt % lower, and up to 20 wt % lower, than the original Noack volatility of the original base oil. In one embodiment the Noack volatility of the base oil is at least 5 wt % lower than the original Noack volatility. In another embodiment the base oil has a Noack volatility less than 18 wt %.

The CCS VIS at −25° C. of the base oil is within 200 mPa·s of the original CCS VIS at −25° C. In one embodiment the CCS VIS at −25° C. of the base oil is within 175, 150, or 125 mPa·s of the original CCS VIS at −25° C. In one embodiment the base oil has a CCS VIS at −25° C. less than 1500 mPa·s. In another embodiment the base oil has a CCS VIS at −25° C. greater than 1100 mPa·s.

In one embodiment the base oil has a boiling range from 700 to 925° F. (371 to 496° C.).

In one embodiment the base oil is made by a process including the additional step of hydrocracking a heavy hydrocarbon feedstock in a hydrocracking zone to obtain a greater amount of the original base oil. The heavy hydrocarbon feedstock has hydrocarbon molecules with a carbon number of C20+, and has a 5 wt % boiling point greater than 600° F. (316° C.). Suitable examples of heavy hydrocarbon feedstocks include vacuum gas oil, deoiled vacuum gas oil, slack wax, Fischer-Tropsch derived waxy feed, petroleum wax, high pour point polyalphaolefin, foots oil, normal alpha olefin wax, deoiled wax, microcrystalline wax, and mixtures thereof.

Hydrocracking

In one embodiment the operating conditions in the hydrocracking zone are those typical of commercial hydrocracking operations. In another embodiment the operating conditions in the hydrocracking zone are selected to convert a heavy hydrocarbon feedstock to a product slate containing greater than 20 wt % or greater than 30 wt % of a waxy intermediate fraction which is upgraded to the original base oil. In different embodiments the operating conditions in the hydrocracking zone can be selected to convert a heavy hydrocarbon feedstock to a product slate containing from greater than 30 wt %, from greater than 32 wt %, or from greater than 34 wt % of a waxy intermediate fraction. In different embodiments the operating conditions in the hydrocracking zone can be selected to convert a heavy hydrocarbon feedstock to a product slate containing less than 60 wt %, less than 50 wt %, less than 40 wt %, or less than 35 wt % of a waxy intermediate fraction. In one embodiment the operating conditions I the hydrocracking zone are selected to convert a heavy hydrocarbon feedstock to a product slate containing from greater than 20 wt %, greater than 25 wt %, or greater than 30 wt % to less than 40 wt % of a waxy intermediate.

The original base oil has an original VI from 95 to 115, an original Noack volatility from 20 to 30 wt %, and an original CCS VIS at −25° C. from 1100 to 1500 mPa·s. The temperature in the hydrocracking zone will be within the range of from about 500° F. (260° C.) to about 900° F. (480° C.), such as within the range of from about 650° F. (345° C.) to about 800° F. (425° C.). A total pressure above 1000 psig is used. For example the total pressure can be above about 1500 psig, or above about 2000 psig. Although greater maximum pressures have been reported in the literature and may be operable, the maximum practical total pressure generally will not exceed about 3000 psig. In some embodiments, more severe hydrocracking conditions such as higher temperature or pressure will result in producing an original base oil product with a higher viscosity index.

Liquid hourly space velocity (LHSV) will usually fall within the range of from about 0.2 to about 5.0, such as from about 0.5 to about 1.5. The supply of hydrogen (both make-up and recycle) is preferably in excess of the stoichiometric amount needed to crack the target molecules and will usually fall within the range of from about 500 to about 20,000 standard cubic feet (SCF) per barrel. In one embodiment the hydrogen will be within the range from about 2000 to about 10,000 SCF per barrel.

The catalysts used in the hydrocracking zone are composed of natural and synthetic materials having hydrogenation and dehydrogenation activity. These catalysts are well known in the art and are pre-selected to crack the target molecules and produce the desired product slate. The hydrocracking catalyst is selected to convert a heavy hydrocarbon feedstock to a product slate containing a commercially significant amount of a waxy intermediate fraction which will be upgraded to the original base oil. Exemplary commercial cracking catalysts generally contain a support consisting of alumina, silica, silica-alumina composites, silica-alumina-zirconia composites, silica-alumina-titania composites, acid treated clays, crystalline aluminosilicate zeolitic molecular sieves, such as zeolite A, faujasite, zeolite X, zeolite Y, and various combinations of the above. The hydrogenation/dehydrogenation components generally consist of a metal or metal compound of Group VIII or Group VIB of the periodic table of the elements. Metals and their compounds such as, for example, cobalt, nickel, molybdenum, tungsten, platinum, palladium and combinations thereof are known hydrogenation components of hydrocracking catalysts.

In one embodiment, the upgrading of the waxy intermediate fraction includes the steps of hydroisomerization dewaxing in an isomerization reactor and hydrofinishing in a hydrofinishing reactor. Hydroisomerization dewaxing and hydrofinishing are well known in the art One example of a suitable upgrading process is described in U.S. Pat. No. 6,337,010, where the isomerization of the waxy intermediate feedstock is carried out at a lower total pressure than the hydrocracking operation.

Base Oil by Process

We provide a base oil having a kinematic viscosity at 100° C. from 4.2 to 4.6 mm$^2$/s, a VI from 105 to 119, and a Noack volatility less than 18 wt % by a process comprising selecting an original base oil and removing a lower boiling fraction. The original base oil has an original VI from 95 to 115, an original Noack volatility from 20 to 30 wt %, and an original CCS VIS at −25° C. from 1000 to 1500 mPa·s. The base oil properties and processes are the same as described earlier. For example, the original base oil may optionally be made by hydrocracking a heavy hydrocarbon feedstock in a hydrocracking zone, wherein the operating conditions in the hydrocracking zone are selected to convert the heavy hydrocarbon feedstock to a product slate containing greater than 20 wt %, greater than 25 wt %, or greater than 30 wt % of a waxy intermediate fraction which is upgraded to the original base oil. In another embodiment, the base oil can have a ratio of Noack volatility to CCS VIS at −25° C. multiplied by 100 from 0.80 to 1.55, from 0.90 to 1.45, or from 0.95 to 1.35.

In one embodiment, the removing is done by selecting a distillation cut point that produces a yield of the base oil that corresponds to a target yield based on a commercial demand for a light neutral base oil. The higher the distillation cut point the lower the yield of light neutral base oil that is produced. This can be an advantage when commercial demand for light neutral base oil is low, yet demand for higher quality base oil is increasing, as it leads to overall better base oil plant profitability. As commercial demand for light neutral base oil changes, the distillation cut point can be selected to meet a new target yield.

In another embodiment, the operating conditions in the hydrocracking zone can also be selected to produce a yield of the base oil that corresponds to the target yield based on commercial demand for light neutral. More severe hydrocracking raises the VI of the waxy intermediate fraction, while cracking more of the waxy intermediate fraction into lower boiling hydrocarbons (some of which will be subsequently distilled out of the original base oil that is produced).

A Method for Predicting a Property of a Base Oil

We provide a method for predicting a property of a base oil that comprises selecting a first base stock and a second base stock. A chart is prepared having a first point that is a first viscometric property under low temperature and a first volatility of the first base stock. The chart also has a second point that is a second viscometric property under low temperature and a second volatility of the second base stock. The first base stock and the second base stock are blended in varying proportions to construct a curve between the first point and the second point on the chart. The curve predicts whether a base oil that is a blend of the first base stock and the second base stock will meet base oil requirements for a finished lubricant. If the curve falls below a point representing the base oil requirements for the finished lubricants, then the base oil blend of the first base stock and the second base stock are capable of making the finished lubricant. If the curve falls above the point representing the base oil requirements for the finished lubricant, then the correct type of a trim stock is ascertained by a direction and a distance one would need to shift the curve.

In one embodiment the finished lubricant is an engine oil. In some embodiments the finished lubricant is a multigrade engine oil, such as 5W-XX, 10W-XX, or 15W-XX, where XX is selected from the group consisting of 20, 30, 40, 50, and 60.

In one embodiment the first and second viscometric properties under low temperature are CCS VIS at −25° C. In another embodiment the first volatility and the second volatility are Noack volatility.

In one embodiment the curve falls above the point representing the base oil requirements for the finished lubricant, and a trim stock is needed to shift the curve below the point. The trim stock is a base oil that has properties that bring the curve in the correct direction. For example, the trim stock may be a Group II, a Group III, or a Group IV base oil; as long as it has desired properties that bring the curve in the correct direction. Generally, less of the trim stock is needed the closer the curve is to the point representing the base oil requirements for the finished lubricant.

In one embodiment, the first base stock, the second base stock, and the trim stock are all Group II. There can be advantages to using all Group II for reducing formulation costs and for simplifying engine oil qualifications.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims.

EXAMPLES

Example 1

Samples of Chevron Neutral Oil 100R were received from the Chevron Richmond Lubricants Oil Plant. Chevron 110RLV base oils were made by vacuum distilling off a lower boiling fraction from the Chevron Neutral Oil 100R. The distillation cut points were approximately 660 to 670° F. The average properties of the Chevron Neutral Oil 100R base oil, and the properties of two different Chevron 110RLV base oils are shown below, in Table I:

TABLE I

| Property | 110RLV Base Oil | 110RLV Base Oil | 100R Base Oil |
|---|---|---|---|
| Viscosity Index | 112 | 118 | 106 |
| SimDist (Wt %), ° F. | | | |
| 0.5 | 668 | 661 | 619 |
| 5 | 713 | 711 | 672 |
| 10 | 727 | 731 | 691 |
| 20 | 745 | 751 | 714 |
| 30 | 760 | 766 | 732 |
| 40 | 773 | 780 | 748 |
| 50 | 785 | 793 | 764 |
| 60 | 797 | 807 | 779 |
| 70 | 810 | 822 | 795 |
| 80 | 825 | 840 | 813 |
| 90 | 844 | 864 | 838 |
| 95 | 859 | 885 | 857 |
| 99.5 | 907 | 945 | 904 |
| Kinematic Vis @100° C., mm$^2$/s | 4.391 | 4.540 | 4.041 |

TABLE I-continued

| Property | 110RLV Base Oil | 110RLV Base Oil | 100R Base Oil |
|---|---|---|---|
| Noack Volatility, wt % | 16.2 | 14.9 | 23.2 |
| CCS VIS at −25° C. | 1367 | 1414 | 1233 |
| Flash Point, COC, ° C. | 216 | 211 | 206 |
| Pour Point, ° C. | −16 | −15 | −14 |
| Oxidator BN, hours | 25.6 | 29.1 | 19.1 |
| Total Aromatics | 0.0675 | 0.0538 | 0.2264 |
| Noack Volatility/CCS VIS at −25° C. × 100 | 1.19 | 1.06 | 1.88 |

The removal of the low boiling fraction of the Chevron 100R gave improvements in a number of different desired base oil properties, including lowering of the Noack volatility, raising of the flash point, lowering of the pour point, increasing of the oxidation stability, and reducing of the aromatics. Another benefit was that the CCS VIS at −25° C. was still maintained well below 1500 mPa·s. Prior to this invention, it had been expected that the removal of the lower boiling fraction would increase the CCS VIS at −25° C. to well above 1700 mPa·s.

Example 2

Others have manufactured base oils having a SUS viscosity at 100° F. of approximately 110, otherwise known as 110N base oils. One example is ConocoPhillips 110N. Another example is a "110N" blended with Fischer-Tropsch derived base oil, Chevron 220R, and Ergon Hygold 100. This example is fully described in U.S. patent application Ser. No. 12/047,887, filed Mar. 13, 2008. Kinematic viscosity in mm$^2$/s at 100° F. can be converted to SUS viscosity at 100° F. according to the arithmetic and the reference table provided in ASTM D 2161-05.

The properties of these two comparison base oils are shown in Table II.

TABLE II

| Typical Property | ConocoPhillips 110N | "110N" Example from 12/047,887 |
|---|---|---|
| Viscosity Index | 95 | 104 |
| Kinematic Vis @100° C., mm$^2$/s | 4.10 | 4.067 |
| Noack Volatility, wt % | 26.5 | 40.56 |
| CCS VIS at −25° C. | 1500 | 1259 |
| Flash Point, COC, ° C. | 199 | — |
| Pour Point, ° C. | −12 | −23 |
| Vol % Distilled at 700° F. | 14 (Max.) | — |
| Noack Volatility/CCS VIS at −25° C. × 100 | 1.76 | 3.22 |

Example 3

Blends of 10W-30 multigrade engine oil were made with blends of different base stocks. They were blended to all have approximately the same kinematic viscosity at 100° C. An additive package was selected that was designed to formulate engine oils meeting both API CJ-4 and ACEA E9 heavy duty engine oil specifications.

The composition of these engine oil blends, and their properties, are described in Table III. The "X"s in the table indicate what base stocks were included in each of the blends.

TABLE III

| Base Stocks, wt % | | Ref. | Blend 1 | Blend 2 | Blend 3 |
|---|---|---|---|---|---|
| Chevron 5R | | >40 | | | |
| Chevron 110RLV | | | X | X | X |
| Chevron 220R | | X | X | X | X |
| Chevron 600R | | X | X | | |
| Chevron 7R | | | | <10 | |
| 6 cSt Group III Base Stock | | | | | <20 |
| Additive Package | | X | X | X | X |
| Properties | Spec. | | Measurements | | |
| Viscosity Index | | 139 | 140 | 140 | 139 |
| Kinematic Vis @100° C., mm²/s | 11.6-12.4 | 12.0 | 12.0 | 12.0 | 12.0 |
| API Gravity | 31(typical) | 31.1 | 30.9 | 31.0 | 31.1 |
| Noack Volatility, wt % | 13(Max) | 12.28 | 12.55 | 12.60 | 12.21 |
| CCS VIS at −25° C. | 5800-7000 | 6453 | 6804 | 6705 | 6603 |
| Pour Point, ° C. | −27(Max) | −34 | −36 | −35 | −35 |
| HTHS, mPa · s | 3.4(Min) | 3.6 | 3.6 | 3.6 | 3.6 |
| MRV @−30° C., mPa · s | 60000(Max) | 18657 | 19974 | 20781 | 19234 |
| Yield Stress | Pass | Pass | Pass | Pass | Pass |
| Scanning Brookfield @ −30° C., mPa · s | | 18657 | 33361 | 32172 | 29805 |
| Gelation Index | 12(Max) | 5.4 | 6.1 | 6.8 | 5.6 |

The Chevron 110RLV gave a technical advantage, in that much lower quantities of the more expensive and highly processed Chevron 5R or Chevron 7R were needed to blend excellent 10W-30 engine oils meeting both API CJ-4 and ACEA E9 heavy duty engine oil specifications. Blend 1 had no Group III base oil or Group IV base oil. Blend 2 had less than 10 wt % Group III or Group IV base oil. Blend 3 had less than 20 wt % Group III or Group IV base oil. Blends 1, 2, and 3 all contained no highly paraffinic unconventional base oil.

Example 4

Figure 1:
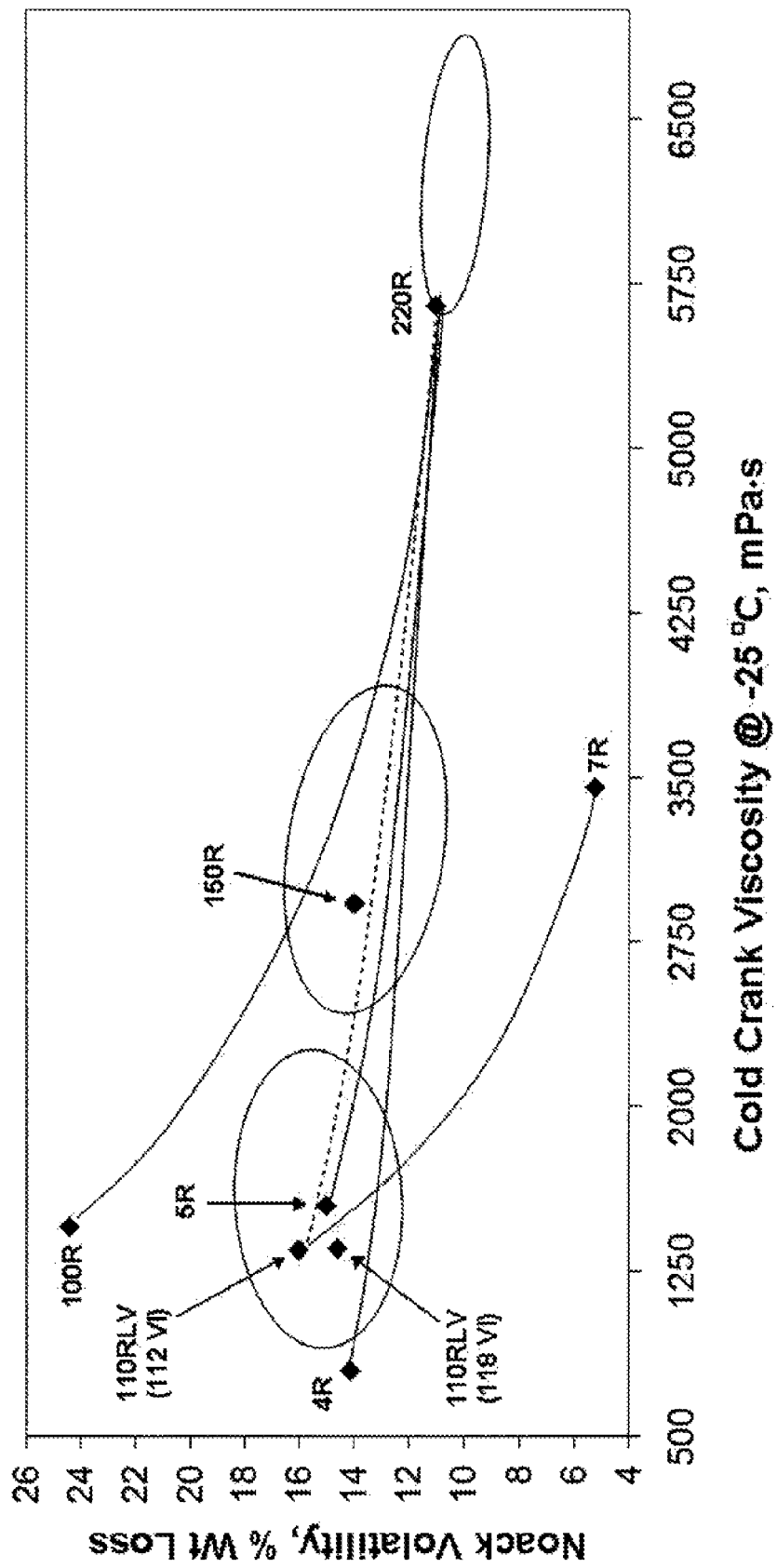
FIG. 1 illustrates lines defining the typical relationship between CCS VIS @-25° C. and Noack volatility of blends of Chevron 100R with Chevron 220R, Chevron 110RLV and Chevron 220R, Chevron 5R and Chevron 220R, Chevron 4R and Chevron 220R, and Chevron 110RLV and Chevron 7R. The circle to the left encompasses the range of CCS VIS and Noack volatility needed for 5W multigrade engine oils. The circle in the center encompasses the range of CCS VIS and Noack volatility needed for 10W multigrade engine oils. The circle to the right encompasses the range of CCS VIS and Noack volatility needed for 15W multigrade engine oils.

The chart shown in FIG. 1 was prepared by selecting different pairs (having a first base stock and a second base stock) of petroleum derived Chevron base stocks, measuring the CCS VIS at −25° C. and the Noack volatility of each base stock and plotting the points (a first point and a second point) on a x-y chart. Blends of the paired Chevron base stocks were made in varying proportions and the CCS VIS at −25° C. and the Noack volatility of each of the blends were measured and used to construct a curve connecting the first and second points.

The chart shown in FIG. 1 also includes points where current commercial multigrade engine oils were tested for CCS VIS at −25° C. and Noack volatility. They tended to cluster into areas on the chart. The area circling the small triangles on the left side of the chart are 5W-XX engine oils, the area circling the small squares in the center of the chart are 10W-XX engine oils, and the area circling the small circles on the right side of the chart are 15W-XX engine oils.

In this example, base oil requirements for a 10W engine oil were set having a CCS VIS at −25° C. of 2800 and a Noack volatility of 14 wt %. The chart in FIG. 1 was referred to, and it was found that the curve between Chevron 110RLV base oil and Chevron 220R base oil fell below and close to the point representing the base oil requirements for the 10W engine oil. This gave a good prediction that the 10W engine oil requirements could be met with a blend of only these two base oils, and not requiring any trim stock.

If it was desired that the engine oil have mostly Chevron 100R and Chevron 220R base oil, then an amount of trim stock would need to be used to meet the same base oil requirements. Based on the chart one would predict that blending in of Chevron 7R trim stock would be a good choice to bring down the Noack volatility of the base oil blend to within the desired range. Based on the chart one would also predict that blending in of Chevron 5R or Chevron 4R trim stock would be a good choice to bring down the CCS VIS at −25° C. of the base oil blend to within the desired range.

Example 5

A target point with a CCS VIS at −25° C. and Noack volatility of 3342 and 11.73 was selected. This target point defined properties that will meet a 10W-XX grade engine oil specification. This target point was placed on a blend chart. Three different base stocks were selected that have CCS VIS at −25° C. and Noack volatilities different from this point, and their CCS VIS at −25° C. and Noack volatilities were placed on the chart. This blend chart is demonstrated in FIG. 2. Curves were drawn between the points defining the CCS VIS at −25° C. and the Noack volatility of each of the three base oils. The curves defined a space inside the curves, where the target point was positioned. This blend chart demonstrates that these three base oils can be used to make a base oil blend having approximately the CCS VIS at −25° C. and Noack volatility of the target point.

FIG. 2 illustrates a blend chart having a first point defined by CCS VIS and Noack volatility of Chevron 100R. The blend chart has a second point defined by the CCS VIS and Noack volatility of Chevron 7R. The blend chart has a third point defined by the CCS VIS and Noack volatility of Chevron 220R. Curves are drawn between the three points to form a ternary blending space. A target point of a CCS VIS of 3350 and a Noack volatility of 11.75 is placed on the chart. This target point is characteristic of a typical 10W-XX finished lubricant product base oil blend. The blend chart instructs a user as to how much of each of the three base oils may be blended to meet the target point properties.

The series of lines constructed between the three edges of the ternary blending space represent three degrees of distance away from each base oil component. For instance, going away from 100R towards the 7R/220R blend curve, a user will encounter three lines along the way that are specific 75%, 50%, and 25% tie-lines between 100R/220R and 100R/7R blend curves.

The composition of each blend component at the target point is defined as a ratio of distances, namely, the distance from the component point to a perpendicular line through the target point divided by the distance from the component point to the opposite edge of the ternary blending space. For example, the amount of 7R in the base oil blend of 100R/220R/7R would be in between 25% and 50% based on the fact that a perpendicular line through the target lies in between the tie-lines that are composed of 50% (closer) and 25% (further away) 7R. A similar process is done for 100R and 220R such that the sum of these compositions is 100%.

We claim:

1. A base oil, comprising:
   hydrocarbons with consecutive numbers of carbon atoms, wherein the base oil has a boiling range from 700 to 925° F. (371 to 496° C.); less than 0.1 wt % total aromatics; an Oxidator BN greater than 22 hours; a flash point greater than 210° C.; a VI from 105 to 119; and a CCS VIS at −25° C. less than 1500 mPa·s.

2. A base oil, comprising:
   hydrocarbons with consecutive numbers of carbon atoms; wherein the base oil has less than 0.1 wt % total aromatics, an Oxidator BN greater than 22 hours, a flash point greater than 210° C., a boiling range from 700 to 925° F. (371 to 496° C.), a CCS VIS at −25° C. of at least 1100 mPa·s, and a ratio of a Noack volatility to a CCS VIS at −25° C. multiplied by 100 from 0.80 to 1.55.

3. The base oil of claim 1 or claim 2, wherein the base oil has a VI from 105 to 115.

4. The base oil of claim 1 or claim 2, wherein the VI is from 107 to 115.

5. The base oil of claim 1, wherein the base oil has a Noack volatility less than 18 wt %.

6. The base oil of claim 2 or claim 5, wherein the Noack volatility is less than 17 wt %.

7. The base oil of claim 1, wherein the VI is from 109 to 114.

8. The base oil of claim 1 or claim 2, wherein the base oil can be blended into a 5W grade, a 10W grade, and a 15W grade engine oil with less than 20 wt % of Group III base oil or Group IV base oil in the blend.

9. The base oil of claim 7, without any Group III or Group IV base oil in the blend.

10. The base oil of claim 1 or claim 2, wherein the base oil can be blended into a 5W grade, a 10W grade, and a 15W grade engine oil with less than 20 wt % highly paraffinic unconventional base oil.

11. The base oil of claim 10, without any highly paraffinic unconventional base oil.

12. The base oil of claim 1 or claim 2, additionally comprising one or more additives to make a finished lubricant.

13. The base oil of claim 12, wherein the finished lubricant is a multigrade engine oil.

14. The base oil of claim 13, wherein the multigrade engine oil is a 5W-XX grade, a 10W-XX grade, or a 15W-XX grade, wherein XX is selected from the group consisting of 20, 30, 40, 50, and 60.

15. The base oil of claim 1 or claim 2, additionally comprising a second base oil.

16. The base oil of claim 15, wherein the second base oil is a Group II base oil.

17. The base oil of claim 15, wherein the second base oil has a kinematic viscosity at 40° C. from 40.00 to 46.00 mm²/s.

18. The base oil of claim 15, wherein the base oil has no Group III or Group IV base oil.

19. The base oil of claim 15, wherein the base oil has a kinematic viscosity at 40° C. from 28.00 to 32.00 mm²/s.

20. The base oil of claim 14, wherein the multigrade engine oil meets an engine oil specification selected from the group of API CJ-4, ACEA E9, or a combination thereof.

* * * * *